United States Patent [19]

Suzuki et al.

[11] Patent Number: 5,042,481
[45] Date of Patent: Aug. 27, 1991

[54] BODY ELECTRODE HOLDER

[75] Inventors: Takashi Suzuki, Soraku; Yosinobu Iguchi, Yamatokoriyama; Yoshihiro Wada, Nara, all of Japan

[73] Assignee: Sharp Kabushiki Kaisha, Osaka, Japan

[21] Appl. No.: 471,408

[22] Filed: Jan. 29, 1990

[30] Foreign Application Priority Data

Jan. 31, 1989 [JP] Japan .............................. 1-11293[U]
Jan. 31, 1989 [JP] Japan .............................. 1-11294[U]
Mar. 30, 1989 [JP] Japan .............................. 1-37444[U]

[51] Int. Cl.⁵ .............................................. A61B 5/04
[52] U.S. Cl. .................................... 128/639; 128/640
[58] Field of Search ............... 128/639, 640, 641, 802, 128/388, 389

[56] References Cited

U.S. PATENT DOCUMENTS

| | | | |
|---|---|---|---|
| 2,943,628 | 7/1960 | Howell | 128/640 |
| 3,380,445 | 4/1968 | Frasier | 128/639 |
| 3,993,049 | 11/1976 | Kater | 128/640 |
| 4,233,987 | 11/1980 | Feingold | 128/639 |
| 4,583,549 | 9/1986 | Manoli | 128/640 |
| 4,852,572 | 8/1989 | Nakahashi et al. | 128/640 |
| 4,865,566 | 9/1989 | Rasmussen | 128/639 |

FOREIGN PATENT DOCUMENTS 63-44010  11/1988  Japan .

Primary Examiner—William E. Kamm
Assistant Examiner—Scott M. Getzow
Attorney, Agent, or Firm—David G. Conlin; Donald Brown; Ronald I. Eisenstein

[57] ABSTRACT

A body electrode holder includes a holding member to be disposed on an outer surface of a living body, and a plurality of perforations formed in predetermined positions of the holding member, through which perforations a plurality of body electrodes pass respectively, the holding member being formed of a sheet material. The predetermined positions correspond to portions of the living body in which portions bioelectricity is to be measured. The body electrode holder makes it possible to a plurality of body electrodes at once and easily to predetermined positions without requiring special technic or knowledge regarding positions to attach the body electrodes.

19 Claims, 8 Drawing Sheets

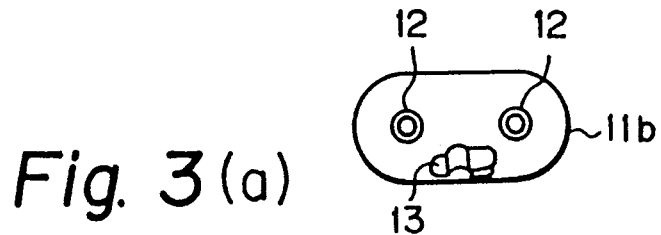
Fig. 3(a)
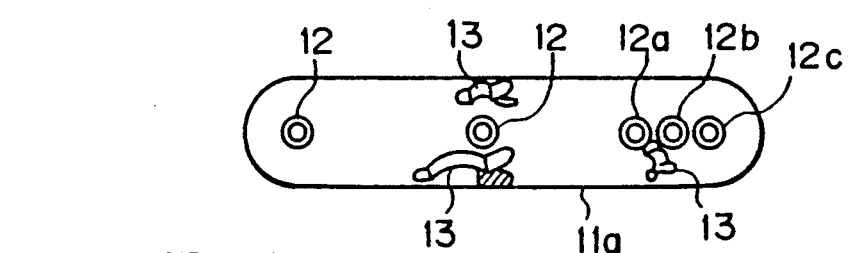
Fig. 3(b)
Fig. 4
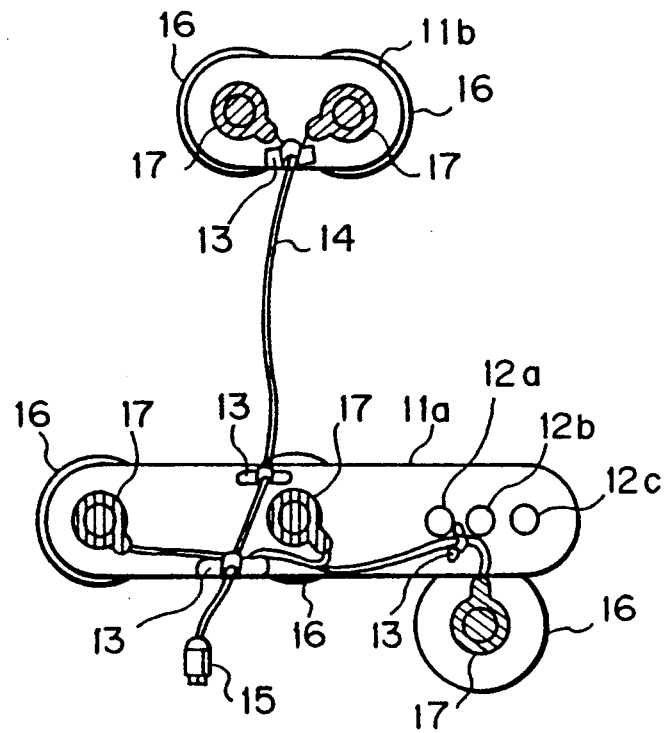

Fig. 5(a)
Fig. 5(b)
Fig. 5(c)
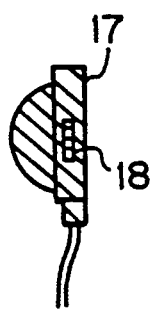
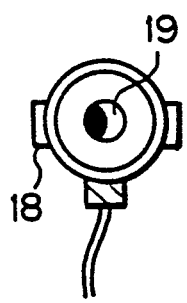
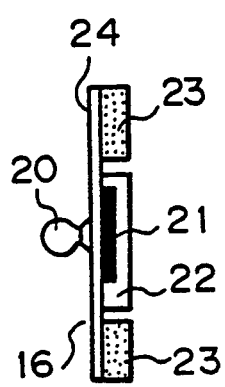
Fig. 6
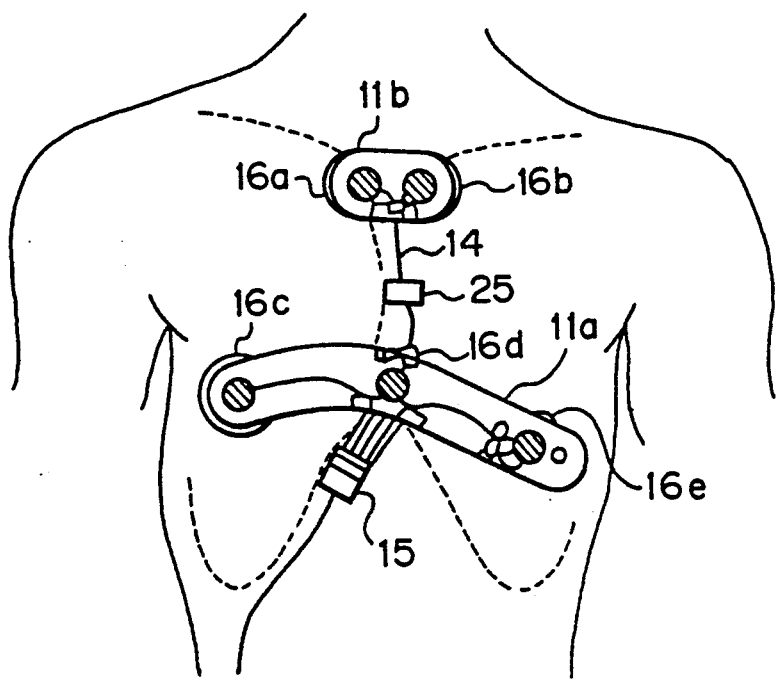

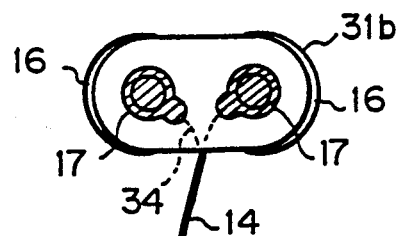
Fig. 7
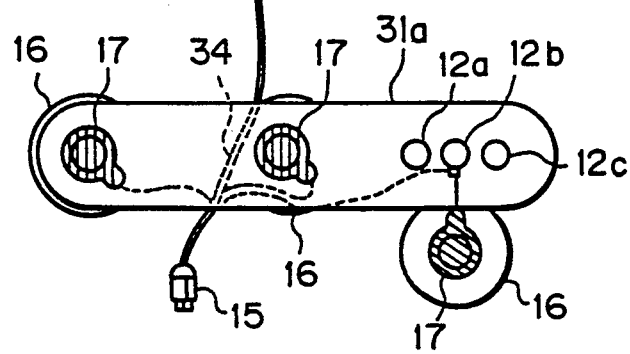
Fig. 8
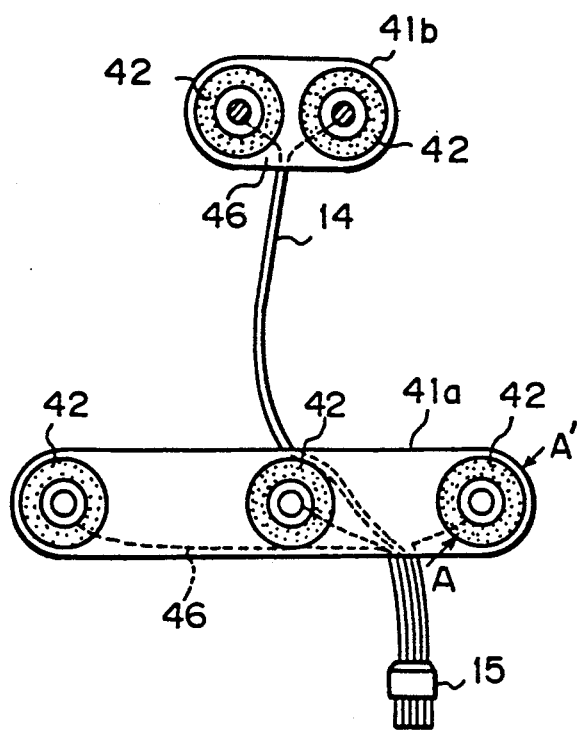
Fig. 9
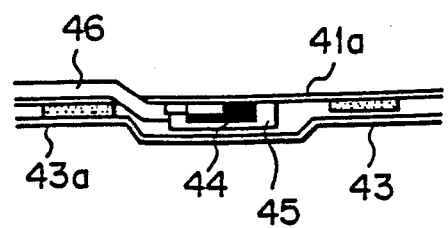

BODY ELECTRODE HOLDER

BACKGROUND OF THE INVENTION

1. Field of the Invention

The present invention concerns a holder for a body electrode used, in particular, for portable electrocardiograph, pulsimeter, etc. and it concerns a holder capable of easily attaching a body electrode to a correct position on a living body and improving the feeling of a patient in use.

2. Description of the Related Art

For measuring bioelectricity, a body electrode comprising an electrode prepared by shaping metal or plastic material and plating silver or silver/silver chloride on the shaped material, and a disc-like adhesive tape for attaching the electrode on a living body is individually attached at a predetermined position of the living body, the electrode is nipped by a clip and detected bioelectricity is sent by way of a lead wire and a connector to an inspection instrument.

However, such a conventional constitution is troublesome since a plurality of body electrodes have to be attached correctly to predetermined positions determined by respective measuring methods, etc., and, in addition, determination for the positions is difficult and requires expert's knowledge. Further, since a plurality of lead wires are used for connecting the respective electrodes to the inspection equipment, they cross with each other, which often leads to erroneous connection, or the lead wires are entangled to each other and pulled to thereby exert unnecessary force on the clip that seizes the electrode. This causes malcontact between the electrode and the clip to generate noises, which lead to incorrect measurement.

In view of the above, lead wires have usually been fixed to a living body by means of a medical tape, etc. but this gives uncomfortable feeling to a patient.

In order to overcome the foregoing problems, Japanese Utility Model Publication 63-44010, as a related invention, discloses a body electrode holder which comprises a holder having a plurality of holding rods disposed side by side and each made of a flexible material insulated at the outer circumferential surface, a fixing portion for fixing a longitudinal end of the holder, a plurality of over-fitting members each of which is fitted over each of the holding rods of the holder, disposed at a predetermined gap and made movable in the longitudinal direction of the holder, and a plurality of body electrodes each disposed between adjacent overfitting members and between the fixing member and the over-fitting member, in which lead wire of the electrode is inserted through the over-fitting member. The body electrode holder is so adapted that a plurality of electrodes can be attached by a single attaching operation and lead wires can be prevented from entangling with each other.

According to the foregoing prior invention, troublesome operation of individually attaching a plurality of body electrodes or disadvantages caused by the crossing and entanglement of the lead wires can be avoided. However, an expert having a knowledge for the attaching position of the body electrode has to properly bend the flexible holder and dispose the body electrode at a predetermined position. Further, electrocardiogram may some time be measured continuously while attaching a portable electrocardiograph to the living body continuously for several days. In such a case the body electrode holder according to the prior art invention also gives a much burden to the patient.

SUMMARY OF THE INVENTION

The object of the present invention is to provide a body electrode holder which can easily attach body electrodes to respective predetermined positions without requiring special technic or knowledge and which can improve the user's feeling at the time when body electrodes are attached.

According to the present invention, the aforementioned object is attained by a body electrode holder including: a holding member to be disposed on an outer surface of a living body, the holding member being formed of a sheet material; and a plurality of perforations formed in predetermined positions of the holding member, through which perforations a plurality of body electrodes pass respectively, the predetermined positions corresponding to portions of the living body in which portions bioelectricity is to be measured.

In accordance with the present invention, a body electrode holding member is constituted with a sheet material in which perforations for attaching the body electrodes are disposed at predetermined positions corresponding to positions of measuring bioelectricity.

Further, the body electrode may be formed integrally to the specific position described above.

Further, for preventing the lead wires connected to the body electrode from crossing with each other, the lead wires may be formed integrally to the sheet material as the holder.

Further, in disposing the body electrode or electrode-attaching perforation to the position for measuring bioelectricity, the sheet material as the holder may be divided into several portions.

Further, a recess for disconnecting the holder into a plurality of portions may be disposed to a portion of the holder, which portion is adjacent to the body electrode.

Furthermore, for adjusting the attaching position of the body electrode, a portion for partially overlapping the holder along the longitudinal or rotational direction of the holder may be disposed to the holder.

In the body electrode holder according to the present invention, since body electrodes are previously disposed integrally, or perforations for attaching the body electrodes are disposed in bioelectricity measuring positions, the holder of the present invention serves as a so-called templet that indicates the measuring positions.

Accordingly, a plurality of body electrodes can be attached all at once and easily to predetermined positions without requiring special technic or knowledge regarding positions to attach the body electrodes.

Further, the holder gives less uncomfortable feeling to the living body and less burden to a user even when it is continuously attached for a long period of time.

Further, since the lead wires are integrated with the holder or bundled at one position, they do not entangle with each other and cause no erroneous connection with the inspection equipment, thus enabling rapid measurement.

Further, since a recess is formed to the holder, the holder can easily be disconnected along the recess after attachment of the holder.

Furthermore, by disposing an adjusting portion to the holder, the distance between the body electrodes can be adjusted depending on the user's figure and, in addition, if the adjusted position is recorded on graduations provided on the holder, any one can attach the holder to the identical positions repeatedly by merely setting the size of the adjusting portion to the recorded value thereby enabling exact measurement.

Further objects and advantages of the present invention will be apparent from the following description of the preferred embodiments of the invention as illustrated in the accompanying drawings

BRIEF DESCRIPTION OF THE DRAWINGS

FIG. 3 is a front elevational view of a body electrode holder as one embodiment of the present invention;

FIG. 3A shows a first body electrode holders and FIG. 3B shows a second.

FIG. 4 is a front elevational view showing a state of mounting the body electrode for using the body electrode holder;

FIG. 5(a) is a side elevational view of an electrode connector;

FIG. 5(b) is a bottom view illustrating the electrode connector,

FIG. 5(c) is a cross sectional view of the body electrode;

FIG. 6 is a front elevational view illustrating the state of the body electrode holder in use;

FIG. 7 is a front elevational view illustrating another embodiment of the present invention in which lead wires are integrate with the holder;

FIG. 8 is a front elevational view illustrating other embodiment of the present invention in which body electrodes are integrated with the holder;

FIG. 9 is a cross sectional view of the body electrode take along a dotted line A—A' of FIG. 8;

DESCRIPTION OF THE PREFERRED EMBODIMENTS

For better understanding of the present invention, prior art will be described while referring to FIGS. 1 and 2.

Figure 1:
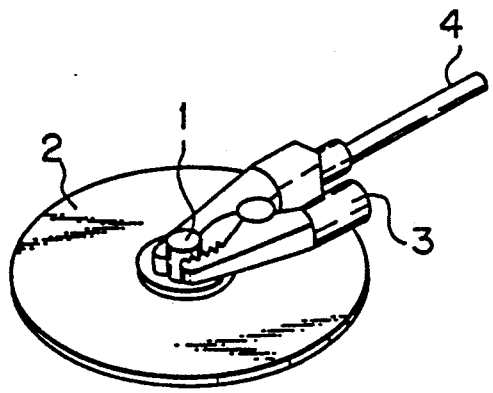
FIG. 1 is a perspective view illustrating a conventional body electrode.
Figure 2:
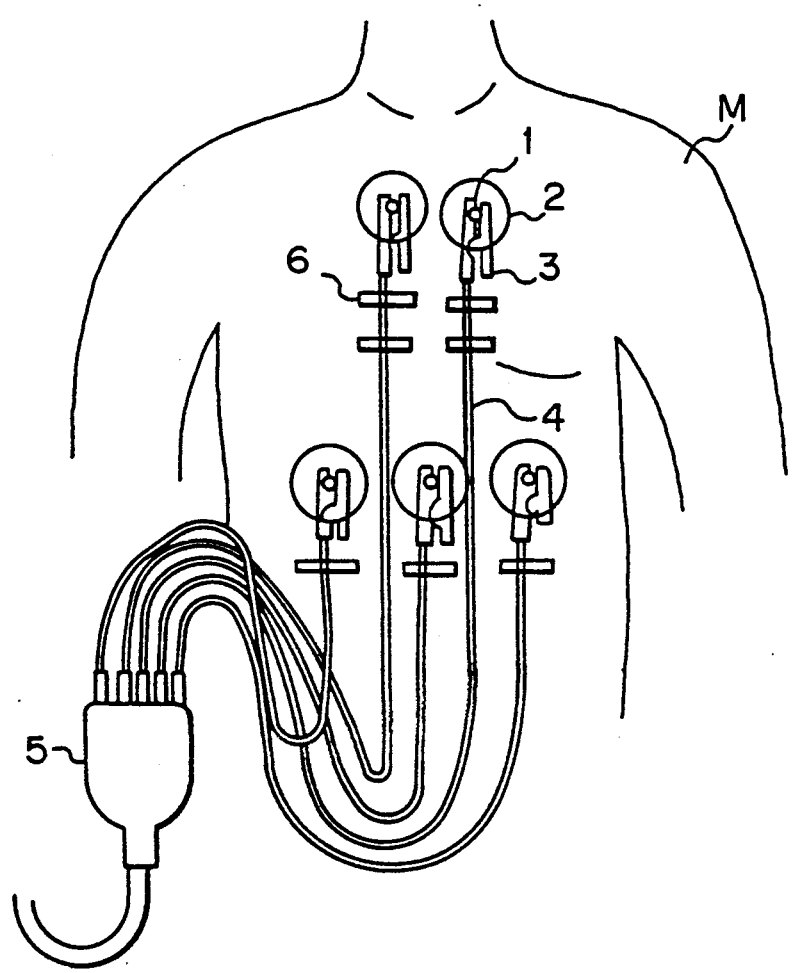
FIG. 2 is a front elevational view showing a state in which the conventional body electrodes are used for measurement.

For measuring the bioelectricity, a body electrode comprising an electrode 1 made of metal or plastic material which is shaped and plated with silver or silver/silver chloride, and a disc-like adhesive tape 2 for attaching the electrode 1 to a living body as shown in FIG. 1 is attached individually to a predetermined position of a living body M as shown in FIG. 2. Then, the electrode 1 is nipped by a clip 3 and detected bioelectricity is sent by means of a lead wire 4 and a connector 5 to a inspection equipment.

Description will be made more in details for embodiments according to the present invention referring to the drawings. In each of the following drawings, those portions or members carrying identical reference numerals represent identical constituent portions and, therefore, duplicate descriptions are omitted.

FIG. 3 shows a front elevational view of a body electrode holder, in which perforations 12 for attaching body electrodes are disposed to holders 11a(FIG. 3(b)), 11b(FIG. 3(a)) .

The holders 11a, 11b are made of material giving less feeling of attachment to a living body upon use such as paper or non-woven fabric. The perforations 12 are perforated at predetermined positions on the holders 11a, 11b in such a manner as to conform with positions for leading out bioelectricity, which portions are determined depending on the measuring method. Then, a plurality of perforations 12a, 12b, 12c (FIG. 3(b)) are disposed to predetermined positions on the holder in such a manner as to correspond to the variation of position for leading out bioelectricity depending on the difference of user's figure. A lead wire holder 13 is disposed at each of suitable positions of the holders 11a, 11b.

When the body electrode holders 11a, 11b according to this embodiment are used, a body electrode 16 shown in FIG. 5(c) and an electrode connector 17 shown in FIG. 5(a) are used.

FIG. 5(c) shows a cross sectional view of a body electrode 16 which comprises a living body contacting portion 22 composed of foamed material such as sponge containing electroconductive gel, an electrode 21 made of electroconductive flexible material such as carbon fiber, electroconductive rubber, silver plated or deposited film, etc., an adhesive 23 (annular fixing portion) disposed around the periphery of the electrode 21 for fixing the electrode portion to the living body, a sheet 24 for securing the electrode, and a snap 20 to be connected to the electrode connector 17.

FIGS. 5(a) and 5(b) show, respectively, the side elevational view and the rear elevational view of the electrode connector 17. A slide portion 19 opens into a complete circle when a knob 18 is picked up and returns to the initial half-opened state by a spring not illustrated when the knob 18 is released. Then, by inserting a snap 20 of the body electrode 16 into the slide portion 19, the snap 20 is nipped by the slide portion 19 and the electrode connector 17 is connected to the electrode 16.

FIG. 4 shows a state in which the body electrodes 16 are respectively mounted to the holders 11a, 11b. The body electrodes 16 are arranged at the back of the holder 11a, 11b (on the side to be brought into contact with the living body). After passing the snap 20 of each of the body electrodes 16 through each of the perforations of the holders 11a, 11b, the snap 20 protruded over the surface of each of the holders 11a, 11bis nipped by the slide 19 of the electrode connector 17. Then, the lead wires 14 are bundled by the lead wire holder 13 and then connected by way of a connector 15 to an inspection equipment not illustrated.

Description will now be made to the method of using the body electrode holder of this embodiment referring to FIG. 6.

At first, the holder 11bis positioned at both of the base ends of a collarbone and the body electrodes 16a, 16b are attached. Then, the body electrode 16d is attached in a position of a stomach pit, the holder 11a is extended rightward and leftward on both sides of the electrode 16d as the center and the body electrodes 16c, 16e are attached. Then, the lead wires 14 are fixed to a living body by means of an adhesive tape 25 and then connected to the inspection equipment by way of the connector 15. In this embodiment, an electrode arrangement of bipolar induction employed in a Holter-electrocardiograph is shown, but the electrode arrangement is different depending on the induction system and, accordingly, an external form of the body electrode holder and the position of the perforation may be changed in accordance with the induction system.

Next, another embodiment is illustrated.

FIG. 7 shows an embodiment not requiring a lead wire holder for bundling lead wires by using lead wires 34 integrated with holders 31a, 31b instead of using lead wire holder in the foregoing embodiment. The lead wire holder and the lead wire may be integrated, for example, by overlaying a paper tape on the surface of each of the holders 31a, 31b and interposing a lead wire between the paper tape and the holder to thereby constitute a laminate structure.

FIG. 8 shows an embodiment in which lead wires 46 and body electrodes (described later) are integrally formed to holders 41a, 41b. This makes the operation of connecting the electrode connector 17 to the body electrode 16 unnecessary, to enable easier measurement.

FIG. 9 shows a body electrode 42 integrated with the holder 41a, in the cross section taken along a line A—A' of FIG. 8. The integrated type body electrode 42 in this embodiment comprises a living body contact portion 45 composed of foamed material such as sponge containing electroconductive gel, an electrode 44 made of electroconductive flexible material such as carbon fiber, electroconductive rubber, silver plated or deposited film, etc., a lead wire 46 made of carbon fiber, copper, stainless steel, etc., and connected to the electrode, and an adhesive 43 disposed at the circumference of the electrode 45 for securing to the living body the electrode portion, and these components are constituted integrally with the holder 41a. In the FIG. 9, 43a represents a protection paper for protecting the adhesive 43, which protection paper is removed at the time when the body electrode 42 is applied to the living body.

Figure 10:
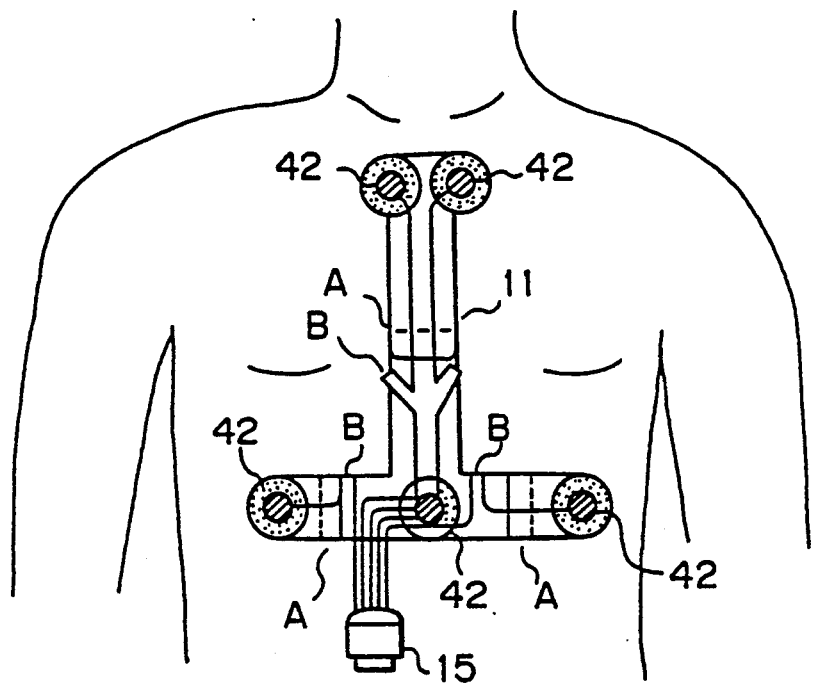
FIG. 10 is a front elevational view illustrating other embodiment of the present invention in which the holder is formed as a sheet in an inverted T-shape configuration.

FIG. 10 shows a further embodiment in which the holder is not divided into two sheets as in the previous embodiment but constituted as a one sheet of holder 11.

For finely adjusting the position of the body electrode 42 depending on the difference of the user's figure, a length adjusting portion A (described later) is provided and the lead wire is slackened at B for preventing the disconnection caused by the adjustment of length.

In a case where the holder is constituted as in this embodiment, since the body electrodes are integrated with the holder at predetermined positions, the user can attach the body electrode more easily.

Figure 12:
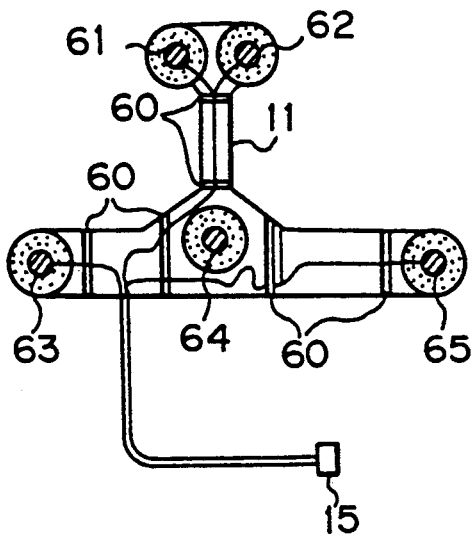
FIG. 12 is a front elevational view of a further embodiment of the present invention in which recesses are disposed to the holder.

In a case where a body is moved while attaching the body electrode for continuous measurement, the attached body electrodes tend to move according to the movement of the body. However, since the positional relationship between the body electrodes is fixed by the holder, the movement of the body electrode is regulated, thereby giving sometime a feeling of constraint or clamping to the user. In view of the above, a further embodiment shown in FIG. 12 is provided. The holder according to this embodiment is so adapted that a holder for fixing the positional relationship between each of the electrodes can easily be disconnected in accordance with the requirement so that each of the body electrodes can freely follow the body movement after attachment of the body electrodes.

Figure 13A:
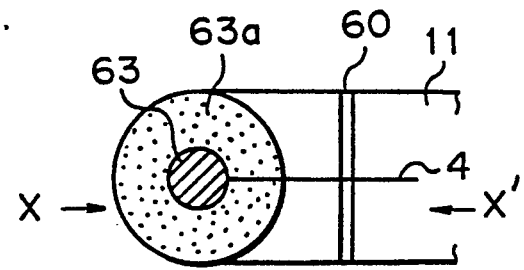
FIG. 13(a) is an enlarged front elevational view illustrating a portion of the holder having the recess.
Figure 13B:
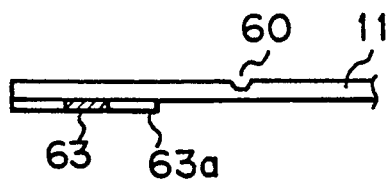
FIG. 13(b) is a cross sectional view taken along a dotted line X—X' of FIG. 13(a)

In this embodiment, recesses 60 are formed at portions of the holder 11, each of which portions is adjacent to a position where each of the body electrodes 61-55 is disposed. As shown in an enlarged view of FIG. 13(a) and a cross sectional view of FIG. 13(b) taken along a line X—X' of FIG. 13(a), each of the recesses 60 is formed by applying recessing the surface of the holder 11. Then, the holder 11 can easily be disconnected, and a portion of holder which portion is situated between two adjacent recesses 60 can be removed along the recess 60 by fingers.

The recessing fabrication may be performed, for example, by using a hot blade adjusted to appropriate temperature and pressure and scanning the surface of the holder, in a case where the holder is made of material capable of being thermally cut. In addition to the recessing fabrication, similar effect can also be obtained by forming a row of perforations in the holder.

With the constitution as in this embodiment, body electrodes can easily be attached to predetermined positions at the time when the body electrodes are applied to the living body and a portion of the holder may be disconnected, as required, along the recesses to be removed, etc. in using the body electrodes, by which the user is free from feeling of constraint or clamping even if he moves his body during continuous attachment of the holder.

Figure 14:
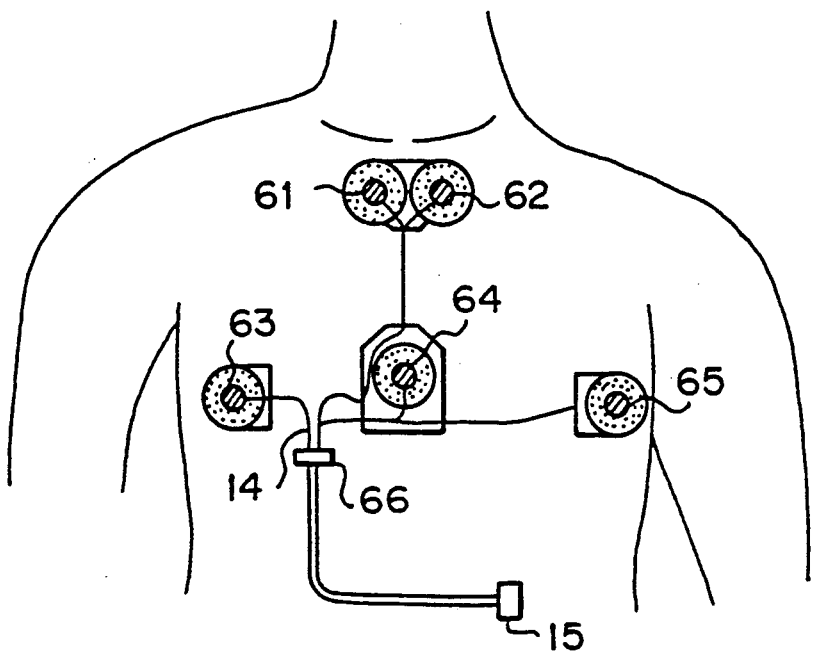
FIG. 14 is a front elevational view illustrating the body electrode holder having the recess shown in FIG. 12 in a state of using a portion of the holder, which portion is remained by cutting the holder along the recess.

Then, FIG. 14 shows a state in which the body electrode holder 11 having the recesses shown in FIG. 12 is attached to the living body and then a portion of the holder 11 is disconnected to be removed along the recess 60. Although body electrodes 61-65 are attached at predetermined positions on the living body, since the holder 11 is disconnected between each of the electrodes, the movement of each of the electrodes 61-65 is not restricted but the electrodes can be freely moved in accordance with the movement of a user's body. Accordingly, the patient can be free from the feeling of constraint or clampling. Reference numeral 66 denotes a tape for securing a lead wire 14 to the living body.

Figure 11A:
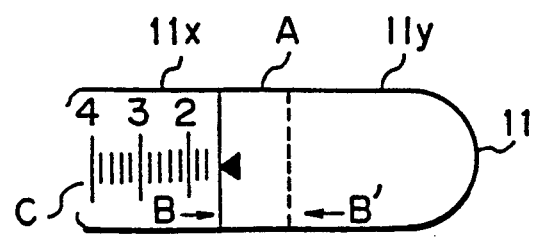
FIG. 11(a) is a plan view showing the adjusting portion for adjusting the length of the holder.
Figure 11B:
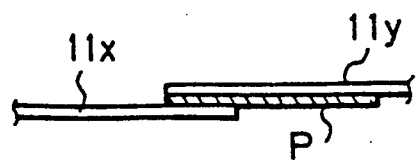
FIG. 11(b) is a cross sectional view illustrating a portion taken along a dotted line B—B' of FIG. 11(a)

FIG. 11(a) shows the front elevational view of the length adjusting portion A and FIG. 11(b) shows the cross sectional view thereof taken along a line B—B' of FIG. 11(a).

The holder 11 is divided into two portions 11x, 11y in the length adjusting portion A, in which the portion 11y is superimposed on the main body 11x of the holder 11 through an adhesive P by which the portion 11y and the main body 11x are bonded to each other. Adjustment for the length is conducted by increasing or decreasing the amount of portions which overlap each other and graduation C is appended as an index to one of portions 11x and 11y. Once the length is adjusted, the positioning can be reproduced again subsequently by merely setting a leading end of the portion 11y to the numerical value on the graduation C.

The method of adjusting length shown in FIG. 11(a) and FIG. 11(b) will be explained referring to FIG. 15 with regard to the case where the method is applied to the body electrode shown in FIG. 8.

Figure 15:
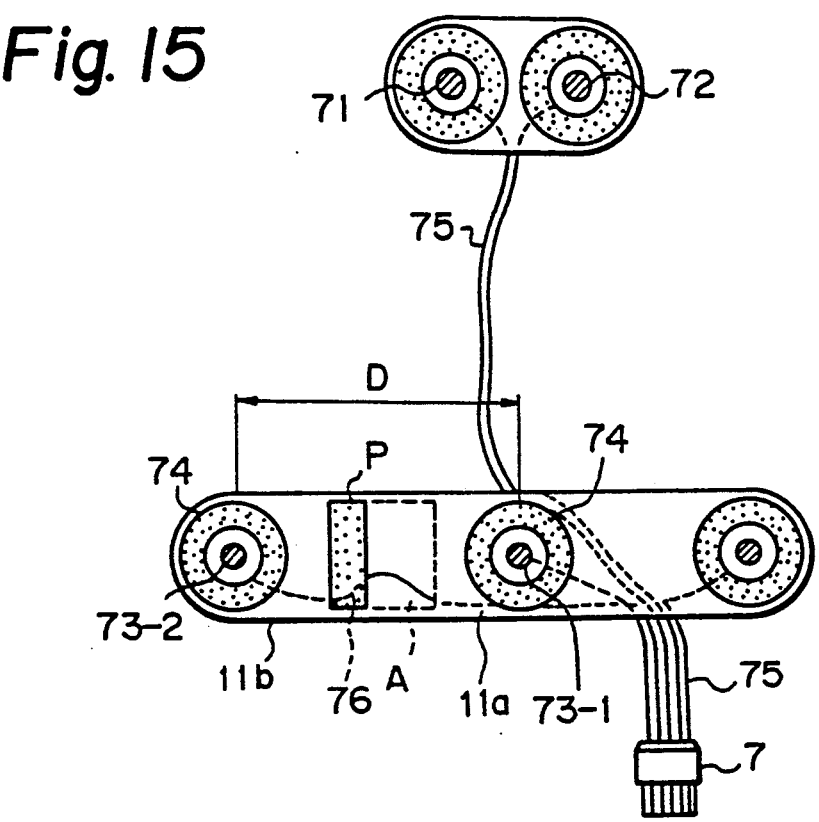
FIG. 15 is a bottom view of a body electrode holder having an adjusting portion.

In FIG. 15, body electrodes 73-1, 73-2 are formed integrally to the holders 11a, 11b respectively. 74 represents an adhesive for attaching the electrode to the living body. Bioelectricity detected from each of the electrodes is sent through the lead wires 75 by way of the connector 7 to an inspection equipment (not illustrated). The position for the electrode 73-2 is adjusted by changing the size of the adjusting portion A. That is, when the adjusting portion A is greater, the distance D between the electrodes 73-1 and 73-2 is shortened, whereas when the adjusting portion A is reduced, the distance D is increased.

For avoiding the lead wires of the electrode 73-2 from disconnection at the time of adjustment, the lead wire is so arranged as to have a slack portion 76.

Figure 18:
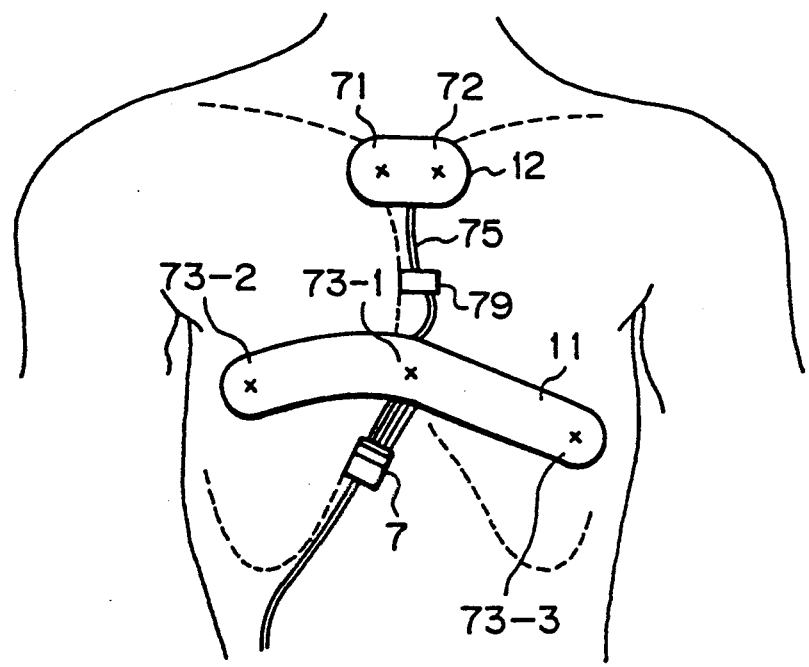
FIG. 18 is a front elevational view showing a state in which the body electrode holder is actually used.

An actual case of using the body electrode holder according to this embodiment will be described referring to FIG. 18.

At first, the holder 12 is disposed on both base ends of a collarbone and the body electrodes 71, 72 are attached to the living body. Then, the body electrode 73-1 is attached to a portion of a stomach pit, the holder 11 is extended rightward and leftward on both sides of the electrode 73-1 as the center and then the body electrodes 73-2, 73-3 are attached to the living body. Then, the lead wire 75 is secured by means of the adhesive tape 79 to the living body and connected by way of an connector 7 to an inspection equipment.

In the foregoing embodiment, the longitudinal distance between the electrodes 73-1 and the 73-2 is adjusted by varying the adjusting portion A of the holders 11a and 11b in the longitudinal direction.

Figure 16A:
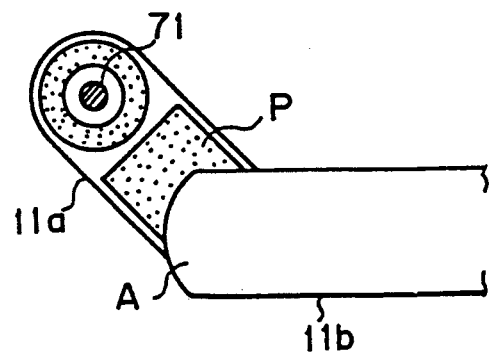
FIG. 16(a) is a top plan view showing other embodiment of the adjusting portion.
Figure 16B:
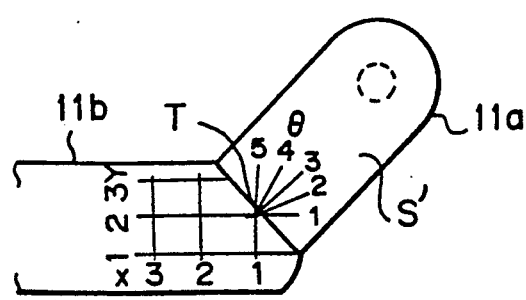
FIG. 16(b) is a bottom view of the adjusting portion shown in FIG. 16(a)
Figure 16C:
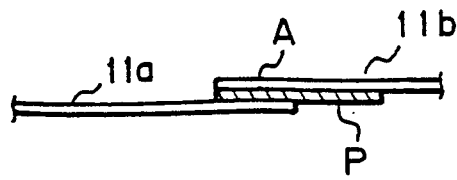
FIG. 16(c) is a cross sectional view of the adjusting portion shown in FIG. 16(a)

Alternatively, the holder 11a can also be displaced rotationally with respect to the holder 11b as shown in FIG. 16. In this case, graduation S' in the direction of $\theta$ is appended to the holder 11a in order to define the size of the adjusting portion A for adjusting a position of the electrode. In the case of this embodiment, the adjusting portion A is defined by an index T as:

$$(X.Y.\theta) = (1.2.1),$$

when the index T takes a coordinate value (1, 2) on X–Y system attached on the holder 11b and the value $\theta = 1$ in which the graduation in the direction of $\theta$ is in parallel with X-axis.

Figure 17A:
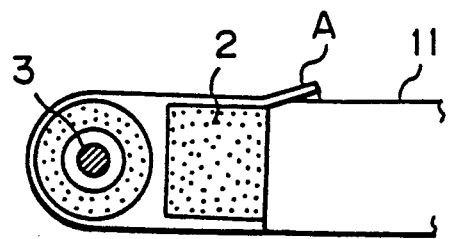
FIG. 17(a) is a top plan view showing a further embodiment of the adjusting portion.
Figure 17B:
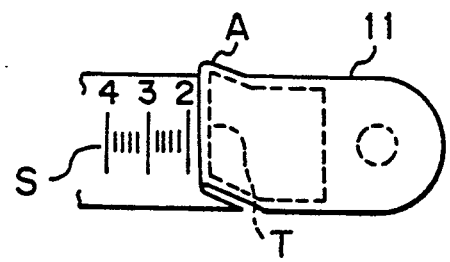
FIG. 17(b) is a bottom view of the adjusting portion shown in FIG. 17(a)
Figure 17C:
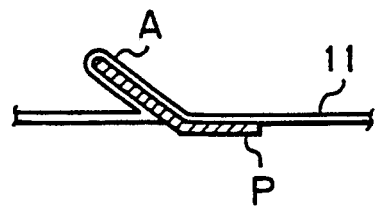
FIG. 17(c) is a cross sectional view of the adjusting portion shown in FIG. 17(a)

FIG. 17 shows a still further embodiment according to the present invention. The holder 11 is continuous and the adjusting portion A is provided by bending the holder 11 in the position of the index T and picking it up by fingers. Then, the size of the adjusting portion A is defined on the basis of the value which the index T takes on the graduation S.

Accordingly, in a case where the adjusting method described above is used for the body electrode holder, the distance between the body electrodes can be adjusted depending on the user's figure and, in addition, if the adjusted position is recorded on graduation, the same attaching position can be obtained repeatedly by any person by merely setting the size of the adjusting portion to the recorded value, whereby exact measurement can be conducted.

Many widely different embodiments of the present invention may be constructed without departing from the spirit and scope of the present invention. It should be understood that the present invention is not limited to the specific embodiments described in the specification, except as defined in the appended claims.

What is claimed is:

1. A body electrode holding device comprising:
   a first electrode holder and a second electrode holder to be disposed on an outer surface of a living body, said first and second electrode holders being formed of a sheet material or non-woven fabric respectively, said second electrode holder being divided into two portions, said two portions capable of being adjusted in the amount in which said two portions overlap each other by increasing or decreasing the amount of overlap to permit adjustment of longitudinal length of said second electrode holder; and
   a plurality of perforations formed in predetermined positions of said first and second electrode holders, through which performations a plurality of body electrodes pass respectively,
   said predetermined positions corresponding to portions of said living body in which portions bioelectricity is to be measured.

2. A body electrode holding device according to claim 1, wherein said first electrode holder attaches a first body electrode, said second electrode holder attaches a second body electrode, said first electrode holder is further provided with a first lead wire holder for fixing to said first electrode holder a first lead wire connected to said first body electrode, and said second electrode holder is further provided with a second lead wire holder for fixing to said second electrode holder a second lead wire connected to said second body electrode.

3. A body electrode holding device according to claim 2, wherein said first lead wire is formed at a first portion thereof integrally with said first electrode holder, said first portion being arranged on said first electrode holder, and said second lead wire is formed at a second portion thereof integrally with said second electrode holder, said second portion being arranged on said second electrode holder.

4. A body electrode holding device according to claim 1, wherein said second electrode holder is provided with recesses disposed transversely at portions of said second electrode holder so as to enable dividing said second electrode holder into a plurality of portions along said recesses, said portions being adjacent to regions where each of said body electrodes is to be arranged.

5. A body electrode holding device according to claim 1, wherein said second electrode holder is divided into two portions so that one of said two portions can be superimposed on the other of said two portions through an adhesive to adjust a longitudinal length of said second electrode holder.

6. A body electrode holding device according to claim 5, wherein said one of said two portions is provided with a graduation so as to define said longitudinal length of said second electrode holder.

7. A body electrode holding device according to claim 1, wherein said two portions are formed to be bonded to each other.

8. A body electrode holding device according to claim 7, wherein said second electrode holder is provided with a graduation so as to define a size of said two portions.

9. A body electrode holding device according to claim 1, wherein each of said body electrodes comprises:
  a living body contacting portion to be contacted with said outer surface for taking out said bioelectricity from said living body, said living body contacting portion being of a disk-like shape;
  an electrode portion received in said living body contacting portion for detecting said taken-out bioelectricity;
  an annular fixing portion concentrically disposed around a periphery of said living body contacting portion for fixing said electrode portion and said living body contacting portion to said living body;
  a circular sheet connected to an annular end face of said living body contacting portion and an annular end face of said annular fixing portion for securing said electrode portion;
  a snap portion connected to said electrode portion in such a manner as to penetrate said circular sheet to thereby protrude in a direction opposite to said electrode portion with respect to said circular sheet, and having an outer diameter capable of being inserted into each of said perforations; and
  an electrode connector adapted to nip said inserted snap portion, and connected to a lead wire for sending said detected bioelectricity to an inspection equipment.

10. A body electrode holding device comprising:
  a first electrode holder, a second electrode holder and a third electrode holder to be disposed on an outer surface of a living body, said first, second and third electrode holders being formed of a sheet material or non-woven fabric respectively, said third electrode holder connected at one end thereof to an intermediate portion of said first electrode holder and connected at the other end thereof to an intermediate portion of said second electrode holder; and
  a plurality of body electrodes
  a plurality of perforations formed in predetermined positions of said first, second and third electrode holders, through which perforations said plurality of body electrodes pass respectively,
  said predetermined positions corresponding to portions of said living body in which portions bioelectricity is to be measured.

11. A body electrode holding device according to claim 10, wherein said first electrode holder attaches a first body electrode, said second electrode holder attaches a second body electrode, said first electrode holder is further provided with a first lead wire holder for fixing to said first electrode holder a first lead wire connected to said first body electrode, and said second electrode holder is further provided with a second lead wire holder for fixing to said second electrode holder a second lead wire connected to said second body electrode.

12. A body electrode holding device according to claim 11, wherein said first lead wire is formed at a first portion thereof integrally with said first electrode holder, said first portion being arranged on said first electrode holder, and said second lead wire is formed at a second portion thereof integrally with said second electrode holder, said second portion being arranged on said second electrode holder.

13. A body electrode holding device according to claim 10, wherein said second and third electrode holders are respectively provided with second and third length adjusting portions for adjusting longitudinal lengths of the respective second and third electrode holders.

14. A body electrode holding device according to claim 13, wherein each of said second and third electrode holders are bent so that they can adjust a longitudinal length.

15. A body electrode holding device according to claim 14, wherein each of said second and third electrode holders is provided with a graduation so as to define a size of each of said second and third length adjusting portions.

16. A body electrode holding device according to claim 10, wherein said second electrode holder is provided with recesses disposed transversely at portions of said second electrode holder so as to enable dividing said second electrode holder into a plurality of portions along said recesses, said portions being adjacent to regions where each of said electrodes is to be arranged, and said third electrode holder is provided with two recesses disposed transversely at portions of said third electrode holder so as to enable disconnecting along said two recesses said third electrode holder from said first and second electrode holders, said portions being adjacent to said first and second electrode holders.

17. A body electrode holding device according to claim 10, wherein said second electrode holder is divided into two portions so that one of said two portions can be superimposed on the other of said two portions through an adhesive to adjust a longitudinal length of said second electrode holder.

18. A body electrode holding device according to claim 17, wherein said one of said two portions is provided with a graduation so as to define said longitudinal length of said second electrode holder.

19. A body electrode holding device according to claim 10, wherein each of said body electrodes comprises:
  a living body contacting portion to be contacted with said outer surface for taking out said bioelectricity from said living body, said living body contacting portion being of a disk-like shape;
  an electrode portion received in said living body contacting portion for detecting said taken-out bioelectricity;
  an annular fixing portion concentrically disposed around a periphery of said living body contacting portion for fixing said electrode portion and said living body contacting portion to said living body;
  a circular sheet connected to an annular end face of said living body contacting portion and an annular end face of said annular fixing portion for securing said electrode portion;

a snap portion connected to said electrode portion in such a manner as to penetrate said circular sheet to thereby protrude in a direction opposite to said electrode portion with respect to said circular sheet, and having an outer diameter capable of being inserted into each of said perforations; and an electrode connector adapted to nip said inserted snap portion, and connected to a lead wire for sending said detected bioelectricity to an inspection equipment.

* * * * *